United States Patent [19]

Greiche et al.

[11] Patent Number: 4,859,459

[45] Date of Patent: Aug. 22, 1989

[54] METHOD OF SHAPING HUMAN HAIR USING DIPROPYLENE GLYCOL MONOMETHYL ETHER

[75] Inventors: Joussef Greiche, Darmstadt; Peter Hartmann, Darmstadt; Joachim Köhler, Reinheim, all of Fed. Rep. of Germany

[73] Assignee: Wella Aktiengesellschaft, Darmstadt, Fed. Rep. of Germany

[21] Appl. No.: 128,827

[22] PCT Filed: Mar. 4, 1987

[86] PCT No.: PCT/EP87/00126

§ 371 Date: Oct. 13, 1987

§ 102(e) Date: Oct. 13, 1987

[87] PCT Pub. No.: WO87/05500

PCT Pub. Date: Sep. 24, 1987

[30] Foreign Application Priority Data

Mar. 12, 1986 [DE] Fed. Rep. of Germany ....... 3608151

[51] Int. Cl.$^4$ .......................... A61K 7/09; A45D 7/04
[52] U.S. Cl. ...................................... 424/71; 132/204; 132/209; 424/72
[58] Field of Search ....................... 424/72, 71; 132/7

[56] References Cited

U.S. PATENT DOCUMENTS

| | | | |
|---|---|---|---|
| 3,654,936 | 4/1972 | Wajaroff | 132/7 |
| 4,177,260 | 12/1979 | Wajaroff | 424/72 X |
| 4,218,435 | 8/1980 | Shiba | |
| 4,424,820 | 1/1984 | Cannell et al. | 424/72 X |

FOREIGN PATENT DOCUMENTS 8705500 9/1987 Fed. Rep. of Germany .
3620849 12/1987 Fed. Rep. of Germany .

OTHER PUBLICATIONS

Chemical Abstracts, vol. 97, 7/1982 (No. 188644t).

*Primary Examiner*—Ellis P. Robinson
*Assistant Examiner*—Susan S. Rucker
*Attorney, Agent, or Firm*—Michael J. Striker

[57] ABSTRACT

The use of dipropylene glycol monomethyl ether in a quantity of 2 to 25 percent by weight as a swelling and penetrating material in hair shaping compositions based on a keratin softening active ingredient or an oxidizing active ingredient.

The use of dipropylene glycol monomethyl ether brings about a clear increase in the effect of hair shaping compositions with an equally good or improved physiological compatibility.

31 Claims, No Drawings

METHOD OF SHAPING HUMAN HAIR USING DIPROPYLENE GLYCOL MONOMETHYL ETHER

DESCRIPTION

The present invention is directed to the use of dipropylene glycol monomethyl ether as a swelling and penetrating material in hair shaping compositions.

In order to permanently shape human hair, the hair is first treated with a hair shaping composition which softens the hair keratin. Alkali hydroxide or reductively acting sulfur compounds, which belong either to the group of sulfites or hydrogen sulfites or to the group of mercaptocarboxylic acids, are generally used for this purpose. These substances are capable of softening the keratin of human hair with respect to its structure and enable a shaping of the hair.

After softening the hair keratin, the hair is rinsed with water and, in the case of a shaping treatment with reductively acting shaping compositions, fixed by means of treating it with a shaping composition based on an oxidizing active ingredient, preferably bromate or hydrogen peroxide. The previously broken disulfide bridge compounds of the hair keratin are reconnected in the new shape given to the hair. The hair is then rinsed with water.

However, the process for permanently shaping hair, described above, has considerable disadvantages. Thus, it is often necessary to use the aforementioned keratin softening active ingredients in relatively high concentrations in order to achieve a sufficient shaping of the hair. In addition, certain keratin softening active ingredients in hair shaping compositions which are adjusted to a pH value of approximately 6, such as sulfites and monothioglycolic acid esters, are only effective to a sufficient degree when temperatures of more than 60 degrees Celsius are applied simultaneously.

The physiological compatibility of the hair shaping compositions employed, however, are considerably impaired by increasing the temperature and concentration of active ingredients. This may result in skin irritations, burn symptoms and, when allowed to act for longer periods, even causticizations of the scalp.

Therefore, one has constantly sought for ways of achieving the greatest possible effectiveness in compositions for the permanent shaping of hair with simultaneous favorable physiological compatibility by means of a corresponding composition and manner of application. As concerns the physiological compatibility, attempts have been made, with reference to the compositions of preparations, to achieve smaller concentrations of active ingredients and to adjust the pH values so as to correspond to the natural pH of the skin and hair. At the same time, with respect to its application, efforts are being made to shorten the time periods during which the compositions are allowed to act and to work at room temperature.

Nevertheless, in order to achieve high effectiveness in such preparations with good physiological compatibility at the same time, certain auxiliary materials, known as swelling and penetrating materials, are often added to these preparations. These substances are capable of helping the active ingredients to penetrate the scleroprotein of the hair and, accordingly, increasing the effectiveness of the preparations in which they are contained.

For example, a good shaping of the hair can be achieved with the use of alkaline preparations by means of the addition of these compounds, even if the shaping compositions contain only a comparatively low concentration of keratin softening active ingredient.

However, the swelling and penetrating materials previously used in compositions for permanently shaping the hair have various disadvantages, so that the results which are achieved are not always satisfactory. Thus, these materials either have poor solubility in water, melamine, for example, or are physiologically incompatible, which is true of formamide, for example. Other materials of this type, such as alkali thiocyanates or ammonium thiocyanates, are decomposed by subsequent oxidizing treatment accompanied by the formation of unwanted by-products, or they are relatively easily saponifiable, as is the case in urea, for example. Alcohols such as isopropanol reduce the compatibility of the compositions with skin.

By way of example, if urea is used in an acidic hair shaping composition (pH =6.0) based on sulfite, the pH value of the composition gradually increases to pH 7 and beyond during storage because of the saponification of the urea accompanied by the formation of ammonium carbonate, so that the shaping effectiveness of the composition is lost. If the urea is used in an alkaline hair shaping composition having a pH value of 12 and based on a mercapto compound, a gradual saponification of the urea accompanied by the formation of ammonium carbonate also occurs. However, in this case, the carbonic acid is linked as a side reaction by the alkali of the composition, and the effectiveness of the hair shaping composition is accordingly reduced as a result of the lowering of the pH value.

It has already been attempted to overcome the aforementioned disadvantages by means of using newer swelling and penetrating materials such as imidazolidin-2-one. In this connection, reference is made to the Applicant's German Patent No. 26 14 723. However, as a result of more recent investigations, doubts have been raised about the physiological compatibility of the imidazolidin-2-one.

Another problem with the process for the permanent shaping of hair, described above, is a poor hold of the hair styling because of insufficient oxidative fixing. All attempts to achieve a rapid and reliable fixing while at the same time maintaining a low concentration of oxidizing active ingredient have been unsatisfactory so far.

Therefore, there arose the problem of how to increase the effect of the aforementioned hair shaping composition without thereby impairing its physiological compatibility.

In continuing the investigation for suitable swelling and penetrating materials it has now been found that by using 2 to 25 percent by weight dipropylene glycol monomethyl ether in hair shaping compositions, according to the present invention, an increased effect relative to previous compositions is achieved both in the acidic and alkaline pH ranges with an equally good or improved physiological compatibility.

Indeed, it is known from G. A. Nowak, Die kosmetischen Praparate (Cosmetic Preparations) (1975), pages 385 and 386, to add dipropylene glycol ether in a concentration of 0.05 to 0.15 percent by weight cold wave solutions as a solubilizer in combination with other solubilizers. The swelling and penetrating promoting effect of the dipropylene glycol monomethyl ether cannot be established in these low concentrations.

The increased effect of the dipropylene glycol monomethyl ether is also surprising because similar glycol ethers, such as propylene glycol monomethyl ether, tripropylene glycol monomethyl ether and diethylene glycol monobutyl ether, cannot bring about such an effect.

The subject matter of the present invention is therefore the use of dipropylene glycol monomethyl ether in a concentration of 2 to 25 percent by weight as a swelling and penetrating material in hair shaping compositions based on a keratin softening active ingredient or an oxidizing active ingredient.

If the hair shaping composition is one based on a keratin softening active ingredient the dipropylene glycol monomethyl ether is preferably used in a quantity of 2 to 15 percent by weight. In hair shaping compositions based on an oxidizing active ingredient, on the other hand, the dipropylene glycol monomethyl ether is preferably used in a concentration of 2 to 10 percent by weight.

The employed dipropylene glycol monomethyl ether is easily soluble in water, physiologically compatible and resistant to reduction, oxidation and saponification.

The permanent shaping of the hair is effected by using reductively acting shaping compositions, normally in two steps. First, the disulfide bridges of the hair keratin are broken by reduction by means of the action of a suitable keratin softening agent. The hair is then given its new shape and rinsed with water. Next, the hair is treated with a hair shaping composition based on an oxidizing active ingredient and is accordingly fixed in its new shape by means of reconnecting the disulfide bridge bonds. The hair is then rinsed with water again in order to remove the excess quantity of oxidizing active ingredient.

The hair shaping compositions used for implementing the first, reductive process step contain cysteine, a cysteine derivative, such as N-acetyl-L-cysteine, thioglycerine, cysteamine or salts of mercaptocarboxylic acids, such as ammonium salts or guanidine salts of thioglycolic acid or thiolactic acid, in a concentration of approximately 2 to 15 percent by weight as keratin reducing active ingredients which act so as to shape the hair. As a rule, these compositions are adjusted so as to be alkaline (pH=7 to 10) in order to enable a softening of the hair and accordingly to enable the hair keratin reducing active ingredient to rapidly penetrate into the interior of the hair. The required alkalinity is achieved for the most part by means of the addition of ammonia, organic amines, ammonium carbonate and alkali carbonate, or ammonium hydrogen carbonate and alkali hydrogen carbonate. But hair shaping compositions which are adjusted so as to be neutral or acidic (pH=6.5 to 7.0) and have an effective content of sulfites or mercaptocarboxylic acid esters can also be taken into consideration. In the former case, it is preferable to use sodium sulfite or ammonium sulfite or the salt of the sulfurous acid with an organic amine, such as monoethanol amine and guanidine, in a concentration of approximately 2 to 10 percent by weight (calculated as $SO_2$). In the latter case, monothioglycolic acid glycol ester or monothioglycolic acid glycerine ester in a concentration of approximately 10 to 40 percent by weight are used in particular.

Mixtures of the aforementioned keratin softening active ingredients can also be used in the hair shaping compositions.

The practical implementation of the permanent hair shaping is generally effected in that the hair is washed, rubbed with a towel, possibly moistened in a preliminary way with a portion of the hair shaping composition, divided into individual strands and wound on rollers. The diameter of the rollers is either approximately 5 to 13 millimeters or approximately 15 to 35 millimeters, depending on whether a permanent wave or a hair straightening is desired. A quantity of shaping composition sufficient for shaping the hair, generally approximately 80 g, is then applied to the wound up hair.

After allowing the composition to act for a period of time sufficient for permanently shaping the hair, which amounts to approximately 5 to 30 minutes depending on the quality of hair, the pH value and the shaping effectiveness of the shaping composition, as well as the application temperature, the shaping composition is rinsed off with water and the hair is fixed oxidatively in a second process step. The hair shaping composition based on an oxidizing active ingredient is used in a quantity of approximately 80 to 100 grams.

For the purpose of fixing, any desired oxidizing active ingredient previously used in hair shaping compositions can be used. Examples of such oxidizing active ingredients are alkali bromates, such as potassium bromate and sodium bromate, or hydrogen peroxide. The concentration of oxidizing active ingredient varies as a function of the application time (generally 5 to 15 minutes) and application temperature. Normally, it is used in a concentration of approximately 0.5 to 10.0 percent by weight. The hair shaping composition based on an oxidizing active ingredient can, of course, contain other conventional additions for such compositions, such as weak acids or peroxide stabilizers.

Next, the rollers are removed, the hair is rinsed out with water and treated further in a conventional manner. As a rule, the hair is set in a water wave after the permanent shaping. In the case of hair straightening, the shaping composition, which acts in an oxidizing manner, can also be rinsed off the hair when it is wound on rollers and the hair can then be dried directly on the rollers without unwinding.

When straightening the hair it is also possible to use strong bases in the shaping compositions, such as lithium-, sodium-, potassium-, guanidine- or tetraalkylammonium hydroxide in a concentration of 2 to 8 percent by weight as keratin softening active ingredient, wherein the hair is then made smooth without the use of rollers by means of repeated combing over the period during which the composition is allowed to act.

Both the hair shaping composition based on a keratin softening active ingredient and the hair shaping composition based on an oxidizing active ingredient can be in the form of an aqueous solution or an emulsion or in thickened form on an aqueous base, particularly as cream, gel or paste. It is also possible to use these compositions in aerosol cans with a propellant under pressure and to dispense them as foam.

Of course, both the hair shaping composition based on a keratin softening active ingredient and the hair shaping composition based on an oxidizing active ingredient can contain all addition materials which are conventional and known for such compositions, for example, thickeners, such as kaolin, bentonite, fatty acids, higher fatty alcohols, starches, polyacrylic acid and its derivatives, cellulose derivatives, alginates, vaseline or paraffin oil, wetting agents or emulsifiers of the categories of anionic, cationic, amphoteric or nonionogenic surface-active substances, such as fatty alcohol sulfates, fatty alcohol ether sulfates, alkyl sulfonates, alkyl benzene sulfates, quaternary ammonium salts, alkyl betaines, oxyethylated fatty alcohols, oxyethylated alkyl phenols, fatty acid alkanol amides or oxyethylated fatty acid esters, as well as clouding agents such as polyethylene glycol ester, or alcohols such as ethanol, propanol, isopropanol or glycerine, solubilizers, stabilizers, buffer substances, perfume oils, dyestuffs, as well as hair conditioning and hair care components such as cationic polymers, lanolin derivatives, cholesterol, pantothenic acid or betaine. The aforementioned components can be contained in these compositions in the quantities which are usual for such purposes, for example, the wetting agents and emulsifiers can be contained in concentrations of approximately 0.2 to 30 percent by weight, while the thickeners can be contained in a quantity of approximately 1.0 to 25 percent by weight.

By means of using dipropylene glycol monomethyl ether in the described hair shaping compositions the effect of these compositions is substantially increased. The reduction of the quantity of keratin softening active ingredients and/or of the pH value (to pH 6.5 to 8.0) which is accordingly made possible allows a hair shaping process which is quick and gentle at the same time. The use of dipropylene glycol monomethyl ether is particularly advantageous in shaping compositions which contain cysteine, sulfite or a salt of thioglycolic acid as keratin softening active ingredient. The pH value of these compositions is preferably 6.5 to 9.5.

As has been shown in comparison tests, the content of active ingredients can be reduced by over 30 percent in shaping compositions based on ammonium thioglycolate as reducing active ingredient by means of adding 10 percent dipropylene glycol monomethyl ether without thereby reducing the waving effectiveness of these compositions.

Moreover, by using dipropylene glycol monomethyl ether in hair shaping compositions containing sulfite, the wave stability can be increased by approximately 20 percent relative to conventional shaping compositions based on sulfite, which contain urea or isopropanol, for example, as swelling and penetrating materials.

The use of dipropylene glycol monomethyl ether in the second step of the hair shaping based on an oxidizing active ingredient, particularly in compositions containing bromate, likewise enables a quicker and more reliable fixing. Feel, ability to comb, curl strength and resiliency of the hair are clearly improved at the same time. The pH value of this hair shaping composition based on bromate is preferably 6.0 to 7.5.

The following examples will explain the subject matter of the invention in more detail without limiting it to these examples.

EXAMPLES

Use in Compositions Based on a Keratin Softening Active Ingredient

Example 1

Use of dipropylene glycol monomethyl ether in a liquid permanent wave composition based on thioglycolate

| | |
|---|---|
| 3.0 g | dipropylene glycol monomethyl ether |
| 21.0 g | ammonium thioglycolate (50 percent aqueous solution) |
| 5.0 g | ammonium hydrogen carbonate |
| 0.8 g | octylphenol oxyethylated with 20 moles ethylene oxide |
| 0.2 g | perfume oil |
| 70.0 g | water |
| 100.00 g | |

The pH value of the solution is 8.0.

The hair is washed with a mild shampoo. Next, the towel-dried hair is pre-moistened with approximately half of the above waving liquid, wound on permanent wave rollers having a diameter of 7 to 10 millimeters, and subsequently moistened with the remaining permanent wave liquid. The hair is then covered with plastic sheeting.

After approximately 15 minutes the wound hair is thoroughly rinsed with water and fixed oxidatively.

Example 2

Use of dipropylene glycol monomethyl ether in a liquid permanent wave composition based on thiolactate

| | |
|---|---|
| 10.0 g | dipropylene glycol monomethyl ether |
| 26.0 g | ammonium thiolactate (50 percent aqueous solution) |
| 3.0 g | n-propanol |
| 0.1 g | benzyl alcohol |
| 0.8 g | cetyltrimethylammonium chloride, 25 percent aqueous solution |
| 60.1 g | water |
| 100.0 g | |

The pH value of the solution is 7.0.

The application of the permanent wave liquid is effected according to example 1.

Example 3

Use of dipropylene glycol monomethyl ether in a permanent wave composition based on thioglycolic acid ester

| | | |
|---|---|---|
| Component A. | 14.0 g | monothioglycolic acid glycerine ester |
| Component B: | 8.0 g | dipropylene glycol monomethyl ether |
| | 0.5 g | stearyl alcohol |
| | 0.1 g | oleyl alcohol |
| | 0.1 g | sodium lauryl sulfate |
| | 0.5 g | stearyl alcohol oxyethylated with 10 moles ethylene oxide |
| | 0.5 g | perfume oil |
| | 90.3 g | water |
| | 100.0 g | |

Immediately prior to use, components A and B are mixed together. The pH value of the ready-to-use preparation is 6.3. The pre-washed and towel-dried hair is wound on permanent wave rollers (diameter 7 to 10 millimeters) and then thoroughly moistened with the entire quantity of permanent wave composition. Further treatment is effected as described in example 1.

Example 4

Use of dipropylene glycol monomethyl ether in a liquid permanent wave composition based on sulfite

| | |
|---|---|
| 11.0 g | dipropylene glycol monomethyl ether |
| 20.0 g | aqueous ammonium sulfite solution (34 percent) |
| 15.6 g | sulfurous acid (with 5 percent $SO_2$ content) |
| 3.0 g | isopropanol |
| 0.1 g | perfume oil |
| 0.2 g | octylphenol oxyethylated with 20 moles ethylene oxide |
| 50.1 g | water |
| 100.0 g | |

The pH value of the solution is 6.7.

The hair is pre-moistened with approximately half of the above permanent wave liquid, wound on rollers and subsequently moistened with the remaining permanent wave liquid. The hair is then covered with a plastic sheeting and heat is supplied for 6 minutes by means of a dryer hood (set to 55 degrees Celsius). The hair is then rinsed with water, oxidatively fixed and further treated as usual.

Example 5

Use of dipropylene glycol monomethyl ether in a hair shaping foam

| | |
|---|---|
| 3.0 g | dipropylene glycol monomethyl ether |
| 23.7 g | ammonium thioglycolate (50 percent aqueous solution) |
| 3.0 g | ammonium carbonate |
| 5.0 g | ammonium hydrogen carbonate |
| 1.5 g | coconut oil acid monoethanol amide |
| 5.0 g | isooctylphenol oxyethylated with 10 moles ethylene oxide |
| 1.5 g | isopropanol |
| 0.2 g | perfume oil |
| 1.0 g | coconut oil acid dimethylaminoacetic acid betaine |
| 56.1 g | water |
| 100.0 g | |

The pH value of the solution is 8.8.

Filling: 94.0 g of the above active ingredient solution are put in a pressurized container together with 0.3 g dinitrogen monoxide and 5.0 g of a 1 : 1 mixture of propane and butane. The internal pressure is 2.7 bar at 20 degrees C.

The washed, towel-dried hair is wound on permanent wave rollers having a diameter of 7 to 10 millimeters. The shaping composition is then foamed on the hair from the pressurized container by means of an application nozzle. After allowing it to act for a period of 15 minutes, the shaping composition is rinsed out of the hair and the hair is fixed oxidatively.

Example 6

Use of dipropylene glycol monomethyl ether in a hair straightening cream based on thioglycolate

| | |
|---|---|
| 6.0 g | dipropylene glycol monomethyl ether |
| 18.0 g | ammonium thioglycolate, 50 percent aqueous solution |
| 3.2 g | ammonia (25 percent) |
| 5.0 g | cetyl alcohol |
| 1.0 g | paraffin oil |
| 4.0 g | oleyl alcohol, oxyethylated with 20 moles ethylene oxide |
| 0.8 g | colloidal silicic acid |
| 0.5 g | perfume oil |
| 61.5 g | water |
| 100.0 g | |

The pH value of the cream is 9.5.

The straightening cream is applied to the hair and evenly distributed. The hair is combed smooth while the composition is allowed to act for a period of 10 minutes. Then, it is rinsed out with water and fixed oxidatively.

Example 7

Use of dipropylene glycol monomethyl ether in a hair straightening cream on an alkaline base

| | |
|---|---|
| 2.0 g | dipropylene glycol monomethyl ether |
| 2.0 g | sodium hydroxide |
| 8.0 g | cetyl stearyl alcohol |
| 1.0 g | sodium lauryl sulfate |
| 5.0 g | kaolin |
| 0.2 g | perfume oil |
| 81.8 g | water |
| 100.0 g | |

The pH value of the cream is 12.8.

The straightening cream is applied to the curly hair and evenly distributed. Then, the hair is combed smooth repeatedly while the composition is allowed to act for a period of approximately 10 minutes and thoroughly rinsed with water.

Use in Hair Shaping Compositions Based on an Oxidizing Active Ingredient

Example 8

Use of dipropylene glycol monomethyl ether in a hair shaping composition containing hydrogen peroxide

| | |
|---|---|
| 2.00 g | dipropylene glycol monomethyl ether |
| 5.00 g | hydrogen peroxide, 50 percent aqueous solution |
| 3.00 g | coconut oil acid amido propyl dimethyl aminoacetic acid betaine, 30 percent aqueous solution |
| 0.10 g | perfume oil |
| 0.30 g | ammonium dihydrogen phosphate |
| 1.0 g | citric acid |
| 0.2 g | ethylenediaminetetraacetic acid |
| 88.4 g | water |
| 100.00 g | |

The pH value of the solution is 2.8.

After rinsing out a hair shaping composition based on a keratin reducing active ingredient, approximately 80 g of the above oxidizing hair shaping composition is foamed on the hair by means of a sponge. After allowing it to act for a period of approximately 5 minutes, it is unwound and the remaining quantity of liquid (20 grams) is evenly distributed on the hair. After approximately 3 minutes, the hair is rinsed with water again.

Example 9

Use of dipropylene glycol monomethyl ether in a hair shaping composition in foam form which contains bromate

| | |
|---|---|
| 6.0 g | dipropylene glycol monomethyl ether |
| 8.0 g | sodium bromate |
| 0.3 g | perfume oil |
| 1.0 g | octylphenol oxyethylated with 20 moles ethylene oxide |
| 84.7 g | water |
| 100.0 g | |

The pH value of the solution is 6.8.
The application is effected according to example 8.

Example 10

Use of dipropylene glycol monomethyl ether in a hair shaping composition in foam form which contains bromate

| | |
|---|---|
| 25.0 g | dipropylene glycol monomethyl ether |
| 9.5 g | sodium bromate |
| 1.7 g | stearic acid diethanolamide |
| 8.0 g | cetyl stearyl alcohol oxyethylated with 30 moles ethylene oxide |
| 1.0 g | coconut oil acid dimethylaminoacetic acid betaine |
| 0.2 g | perfume oil |
| 54.6 g | water |
| 100.0 g | |

The pH value of the preparation is 6.3.

Filling: 93.5 g of the above active ingredient solution are put in a pressurized container together with 0.5 g dinitrogen monoxide and 6.0 g isobutane. The internal pressure is 2.7 bar at 20 degrees C.

After rinsing out a hair shaping composition based on a keratin reducing active ingredient, the above oxidizing hair shaping composition is foamed onto the hair from the pressurized container by means of an application nozzle. After approximately 10 minutes, the hair is removed from the rollers and subsequently treated with an amount of foam. After another 3 minutes the hair is thoroughly rinsed.

We claim:

1. A method of shaping human hair which comprises the steps of:
   (a) washing the hair;
   (b) towel-drying the hair;
   (c) dividing the hair into individual streams and winding the hair upon rollers;
   (d) applying to the hair a hair shaping composition comprising:
      (i) a keratin-softening reducing agent in an amount effective to break disulfide bonds in hair keratin; and
      (ii) 2 to 25% by weight of dipropylene glycol monomethyl ether as a swelling agent and a penetrating material;
   (e) allowing the hair shaping composition to act for a period of time sufficient to permanently shape the hair;
   (f) rinsing the shaping composition from the hair with water;
   (g) applying to the hair a fixing composition which comprises an oxidizing agent in an amount effective to reconnect the disulfide bonds broken during step (d);
   (h) allowing the oxidizing agent to act for a period of time sufficient to fix the shape of the hair; and
   (i) removing the rollers from the hair and rinsing the fixing composition from the hair.

2. The method of shaping human hair defined in claim 1, wherein according to step (d) the keratin-softening reducing agent is cysteine, N-acetyl-cysteine, thioglycerine, cysteamine, or a salt of a mercaptocarboxylic acid selected from the group consisting of ammonium or guanidine salts of thioglycolic acid and thiolactic acid.

3. The method of shaping human hair defined in claim 1, wherein according to step (d) the keratin-softening reducing agent is an ester of a mercapto-carboxylic acid.

4. The method of shaping human hair defined in claim 1 wherein according to step (d) the keratin-softening reducing agent is a sulfite salt or a strong base.

5. The method of shaping human hair defined in claim 2 wherein the salt of the mercaptocarboxylic acid is the ammonium salt of the thioglycolic or thiolactic acid.

6. The method of shaping human hair defined in claim 3 wherein the ester of a mercaptocarboxylic acid is the monothioglycolic acid glycol ester or monothioglycolic acid glycerine ester.

7. The method of shaping human hair defined in claim 4 wherein the sulfite salt is ammonium sulfite, sodium sulfite, or the sulfite salt produced by the reaction of sulfurous acid and monoethanolamine or guanidine, used in a concentration of 2 to 10% by weight.

8. The method of shaping human hair defined in claim 4 wherein the strong base is selected from the group consisting of lithium hydroxide, sodium hydroxide, potassium hydroxide, tetraalkyl ammonium hydroxide, and guanidine hydroxide.

9. The method of shaping human hair defined in claim 2 wherein the keratin-softening reducing agent comprises 2 to 15% by weight of the hair shaping composition.

10. The method of shaping human hair defined in claim 2 wherein the sulfite salt is used in a quantity of 2 to 10% by weight of the shaping composition.

11. The method of shaping human hair defined in claim 3 wherein the ester of a mercapto carboxylic acid is used in a quantity of 10 to 40% by weight of the hair shaping composition.

12. The method of shaping human hair defined in claim 1 wherein the shaping is hair straightening.

13. The method of shaping human hair defined in claim 1 wherein the shaping involves applying a permanent wave to the hair.

14. A method of straightening human hair which comprises the steps of:
   (a) washing the hair;
   (b) towel-drying the hair;
   (c) applying to the hair a hair straightening composition which comprises:
      (i) 2 to 8% by weight of a keratin-softening, strongly basic reducing agent selected from the group consisting of lithium hydroxide, sodium hydroxide, potassium hydroxide, tetraalkyl ammonium hydroxide and guanidine hydroxide to break disulfide bonds in the hair keratin; and
      (ii) 2 to 25% by weight of dipropylene glycol monomethyl ether as a swelling agent and a penetrating material;
   (d) allowing the hair straightening composition applied during step (c) to act for a period of time sufficient to straighten the hair while at the same time repeatedly combing the hair;
   (e) rinsing the hair straightening composition from the hair with water;
   (f) applying to the hair a fixing composition which comprises an amount of an oxidizing agent effective to reconnect the disulfide bonds broken during step (c);
   (g) allowing the oxidizing agent to act for a period of time sufficient to fix the straightened hair; and
   (h) rinsing the fixing composition from the hair.

15. A method of shaping human hair which comprises the steps of:

(a) washing the hair;
(b) towel-drying the hair;
(c) dividing the hair into individual streams and winding the hair upon rollers;
(d) applying to the hair a hair shaping composition comprising a keratin-softening reducing agent in an amount effective to break disulfide bonds in hair keratin;
(e) allowing the hair shaping composition to act for a period of time sufficient to permanently shape the hair;
(f) rinsing the shaping composition from the hair with water;
(g) applying to the hair a fixing composition which comprises:
  (i) an oxidizing agent in an amount effective to reconnect the disulfide bonds broken during step (d); and
  (ii) 2 to 25% by weight of dipropylene glycol monomethyl ether as a swelling agent and a penetrating material;
(h) allowing the oxidizing agent to act for a period of time sufficient to fix the shape of the hair; and
(i) removing the rollers from the hair and rinsing the fixing composition from the hair.

16. The method of shaping human hair defined in claim 15 wherein the oxidizing agent applied to the human hair according to step (g) is selected from the group consisting of hydrogen peroxide and an alkali metal bromate.

17. The method of shaping human hair defined in claim 15 wherein the oxidizing agent applied to the human hair according to step (g) is used in an amount of 0.5 to 10% by weight of the fixing composition.

18. In a process for the shaping of human hair wherein the human hair is shaped by treatment with a reducing agent to break disulfide bonds in the hair keratin, the reducing agent is removed from the hair, an oxidizing agent is then applied to reconnect the broken disulfide bonds thereby fixing the shape of the hair, and then the oxidizing agent is removed from the hair, the improvement which comprises the step of:
  adding to the reducing agent in an amount of 2 to 25% by weight of the resulting hair shaping composition, dipropylene glycol monomethyl ether as a swelling agent and a penetrating material.

19. In a process for the shaping of human hair wherein the human hair is shaped by treatment with a reducing agent to break disulfide bonds in the hair keratin, the reducing agent is removed from the hair, an oxidizing agent is then applied to reconnect the broken disulfide bonds thereby fixing the shape of the hair, and then the oxidizing agent is removed from the hair, the improvement which comprises the step of:
  adding to the oxidizing agent in an amount of 2 to 25% by weight of the resulting hair fixing composition, dipropylene glycol monomethyl ether as a swelling agent and a penetrating material.

20. A cosmetic composition based on a keratin-softening active ingredient which comprises:
  (a) a keratin-softening reducing agent in an amount effective to break disulfide bonds in hair keratin; and
  (b) 2 to 25% by weight of dipropylene glycol monomethyl ether as a swelling agent and a penetrating material.

21. The cosmetic composition defined in claim 20 wherein the keratin-softening reducing agent is selected from the group consisting of a salt or ester of a mercaptocarboxylic acid, cysteine, thioglycerine, cysteamine, a sulfite or a strong base.

22. The cosmetic composition defined in claim 21, wherein the salt of the mercaptocarboxylic acid is selected from the group consisting of the ammonium salt of a thioglycolic acid or the ammonium salt of thiolactic acid.

23. The cosmetic composition defined in claim 21, wherein the ester of a mercaptocarboxylic acid is selected from the group consisting of monothioglycolic acid glycol ester and monothioglycolic acid glycerine ester.

24. The cosmetic composition defined in claim 21, wherein the sulfite is selected from the group consisting of ammonium sulfite, sodium sulfite, and the salts of sulfurous acid with organic amines.

25. The cosmetic composition defined in claim 21, wherein the strong base is selected from the group consisting of lithium hydroxide, sodium hydroxide, potassium hydroxide, guanidine hydroxide, and tetraalkyl ammonium hydroxide.

26. The cosmetic composition defined in claim 21, wherein the salt of the mercaptocarboxylic acid, the thioglycerine, the cysteamine, and the cysteine, are contained in a quantity of 2 to 15% by weight.

27. The cosmetic composition defined in claim 21, wherein the sulfite and the strong base are contained in a quantity of 2 to 10% by weight.

28. The cosmetic composition defined in claim 21, wherein the mercaptocarboxylic acid ester is contained in a quantity of 10 to 40% by weight.

29. A cosmetic composition based on an oxidizing agent as active ingredient, which comprises:
  (a) an oxidizing agent in an amount effective to reform a cleaved disulfide linkage in hair keratin, said hair keratin having been previously treated with a reducing agent to cleave the disulfide linkage; and
  (b) 2 to 25% by weight of dipropylene glycol monomethyl ether as a swelling agent and a penetrating material.

30. The cosmetic composition defined in claim 29 wherein the oxidizing agent is selected from the group consisting of hydrogen peroxide and alkali bromate.

31. The cosmetic composition defined in claim 29 wherein the oxidizing agent is contained in a quantity of 0.5 to 10% by weight.

* * * * *